United States Patent
Wehner et al.

(10) Patent No.: US 6,794,517 B2
(45) Date of Patent: Sep. 21, 2004

(54) BIS(TRIFLUOROMETHYL)HYDANTOINS AS INTERMEDIATES FOR PHARMACEUTICALLY ACTIVE INGREDIENTS

(75) Inventors: Volkmar Wehner, Sandberg (DE); Hans Ulrich Stilz, Frankfurt (DE); Klaus Burger, Leipzig (DE); Alexander Golubev, Moscow (RU); Sergej Ossipov, Mytischi (RU)

(73) Assignee: Aventis Pharma Deutschland GmbH, Frankfurt (DE)

(*) Notice: Subject to any disclaimer, the term of this patent is extended or adjusted under 35 U.S.C. 154(b) by 0 days.

(21) Appl. No.: 10/092,889

(22) Filed: Mar. 8, 2002

(65) Prior Publication Data

US 2002/0183374 A1 Dec. 5, 2002

(30) Foreign Application Priority Data

Mar. 10, 2001 (DE) .......................... 101 11 876

(51) Int. Cl.$^7$ ............................................. C07D 233/72
(52) U.S. Cl. ................ 548/319.5; 548/319.1; 548/320.1
(58) Field of Search .......................... 548/316.7, 319.1, 548/319.5, 320.1

(56) References Cited

U.S. PATENT DOCUMENTS

| | | | |
|---|---|---|---|
| 5,939,556 A | 8/1999 | Zoller et al. | |
| 6,034,238 A | 3/2000 | Wehner et al. | |
| 6,331,552 B1 | 12/2001 | Wehner et al. | |

FOREIGN PATENT DOCUMENTS

| | | |
|---|---|---|
| EP | 0 903 353 A1 | 3/1999 |
| EP | 0 905 139 A2 | 3/1999 |
| EP | 0 918 059 A1 | 5/1999 |
| WO | WO 96/33976 A1 | 10/1996 |
| WO | WO 99/60015 A1 | 11/1999 |

OTHER PUBLICATIONS

E.E. Büllesbach "Schutzgruppen in der Peptidsynthese (Teil 2): Mehrfunktionelle Aminosäuren—zur Abspaltung—Perspektiven der Schutzgruppentechnik", Kontakte (Merck), 1980, pp. 23–35, No. 1.

W. Duczek et al., "A Simple and Convenient Synthesis of N–Formly Amino Acid Esters Under Mild Conditions", Synthesis, Jan. 1996, pp. 37–38.

A. Hubbuch et al., "Schutzgruppen in der Peptidsynthese (Teil 1): Schutzgruppentaktik, Amino– und Carboxyl–Schutzgruppen", Kontakte (Merck),1979, pp. 14–23, No. 3.

Wolfgang Steglich et al., "Eine einfache Synthese für N–Acylimine des Hexafluorund symm. Dichlortetrafluoracetons", Chem. Ber., 1974, pp. 1488–1498, No. 107.

*Primary Examiner*—Ceila Chang
*Assistant Examiner*—Sonya Wright
(74) *Attorney, Agent, or Firm*—Heller Ehrman White and McAuliffe LLP

(57) ABSTRACT

The present invention relates to hydantoins of formula I,

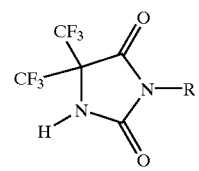

in which R is the residue of an amino carboxylic acid or of an amino carboxylic acid derivative, which is obtained formally by removing an $NH_2$ group from an amino carboxylic acid or an amino carboxylic acid derivative, to the preparation thereof and to the use thereof as intermediates, in particular for preparing pharmaceutically active ingredients.

13 Claims, No Drawings

BIS(TRIFLUOROMETHYL)HYDANTOINS AS INTERMEDIATES FOR PHARMACEUTICALLY ACTIVE INGREDIENTS

This application claims priority to German Patent Application 10111876.7, filed Mar. 10, 2001, which is hereby incorporated by reference, in their entirety. All references cited below, including patents, patent applications and scientific journals and books also are herein incorporated by reference in their entirety.

BACKGROUND OF THE INVENTION

The present invention relates to hydantoins of formula I,

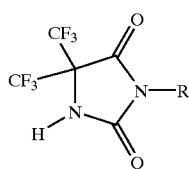

I wherein R is a residue of an amino carboxylic acid or of an amino carboxylic acid derivative, which is obtained formally by removing an NH$_2$ group from an amino carboxylic acid or an amino carboxylic acid derivative. The present invention also relates to the preparation of such hydantoins and the use thereof as intermediates, particularly for preparing pharmaceutically active ingredients.

DESCRIPTION OF PRIOR ART

Various patent documents, for example U.S. Pat. No. 6,331,552 B, U.S. Pat. No. 6,034,238, EP-A-903353, EP-A-905139, EP-A-918059 and WO-A-99/60015, describe pharmaceutically active substituted hydantoins, which are inhibitors of the adhesion and migration of leukocytes and/or antagonists of the adhesion receptor VLA-4, which belongs to the integrin group, and are suitable, for example, for treating disorders such as rheumatoid arthritis, asthma, allergies, multiple sclerosis or atherosclerosis. In addition, these documents disclose various methods of synthesizing hydantoins using different starting compounds and proceeding via different intermediates. In these methods, it is possible, for example, to first assemble a hydantoin intermediate in which the ring nitrogen atoms do not carry substituents, i.e., they carry hydrogen atoms, and then introduce onto the nitrogen atoms of the hydantoin ring substituents, which can subsequently be modified. It is also possible to utilize starting compounds that contain substituents already bonded to nitrogen atoms in assembling hydantoin intermediates, which substituents then appear in the hydantoin intermediate. Certain hydantoins as intermediates for preparing pharmaceutically active ingredients are described in WO-A-96/33976.

In particular, it has now proved advantageous to utilize the hydantoins of formula I, which have not previously been described, as intermediates for preparing a group of certain pharmaceutically active hydantoins (=2,5-dioxoimidazolidines) that carry two trifluoromethyl groups as substituents on the carbon atom in the 4-position and are distinguished by a particularly favorable profile of properties.

SUMMARY

The present invention encompasses hydantoins of formula I:

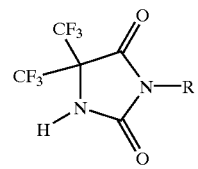

I wherein R is a residue of an amino carboxylic acid or of an amino carboxylic acid derivative, which is obtained formally by removing an NH$_2$ group from an amino carboxylic acid or an amino carboxylic acid derivative, or salts thereof, or stereoisomers thereof, or tautomers thereof.

The present invention also encompasses a process for preparing the hydantoin of formula I

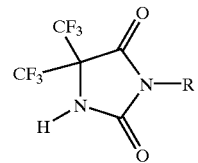

I which comprises reacting the compound of formula II with a compound of formula III

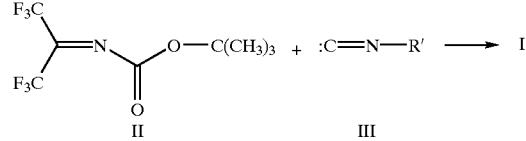

wherein R' in formula III is defined as R in formula I, but wherein free carboxylic acid groups are present in the compounds of formula III in esterified form.

The invention further encompasses a process for preparing a pharmaceutically active ingredient derived from a hydantoin of formula I

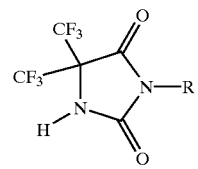

I preferably comprising a 2,5-dioxo-4,4-bis(trifluoromethyl) imidazolidine ring, which comprises reacting the compound of formula I at a functional group in the residue R with another synthetic building block.

DETAILED DESCRIPTION OF THE PREFERRED EMBODIMENTS

The present invention encompasses hydantoins of formula I:

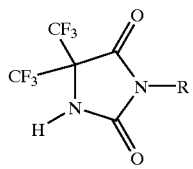

wherein R is a residue of an amino carboxylic acid or of an amino carboxylic acid derivative, which is obtained formally by removing an $NH_2$ group from an amino carboxylic acid or an amino carboxylic acid derivative, or the salts thereof, or stereoisomers thereof, or tautomers thereof. Accordingly, the compounds of formula I contain at least one carboxylic acid group COOH or a derivative thereof in the residue R.

Amino carboxylic acid derivatives include compounds that are obtained formally from the relevant amino carboxylic acid by converting one or more carboxylic acid groups into other groups directly related to the carboxylic acid group. Amino carboxylic acid derivatives can be, for example, ester groups, amide groups, nitrile groups, aldehyde groups and hydroxymethyl groups. Preferably, the amino carboxylic acid derivatives are ester groups, such as, for example, $(C_1-C_6)$-alkyl esters or phenyl-$(C_1-C_4)$-alkyl esters. Preferred ester groups include, for example, methyl esters, ethyl esters, propyl esters (e.g., n-propyl esters and isopropyl esters), butyl esters (e.g, n-butyl esters, isobutyl esters, sec-butyl esters and tert-butyl esters), pentyl esters, hexyl esters, and benzyl esters. Preferred amide groups include, for example, unsubstituted amides ($CONH_2$), N—$(C_1-C_4)$-alkylamides and N,N-di-$((C_1-C_4)$-alkyl) amides, such as N-methylamides and N,N-dimethylamides, N-methoxy-N-methylamides and N-benzylamides.

The amino carboxylic acid or derivative of the formula $H_2N$—R, from which the residue R in formula I is derived, may be a natural or unnatural amino carboxylic acid or a derivative of a natural or unnatural amino carboxylic acid. In addition to the one or more carboxylic acid groups or derivatives of carboxylic acid groups that include ester groups, amide groups, nitrile groups, aldehyde groups or hydroxymethyl groups, the residue R or the amino carboxylic acid or the amino carboxylic acid derivative, from which the residue R is derived, may contain one or more other functional groups. All functional groups and carboxylic acid groups and derivatives of carboxylic acid groups may be present in protected form. Suitable protective groups include, but are not limited to, urethane protective groups, carboxylic acid protective groups and side-chain protective groups, which are described in Hubbuch, Kontakte (Merck) 1979, No. 3, pages 14 to 23, and in Bullesbach, Kontakte (Merck) 1980, No. 1, pages 23 to 35. As examples, the following are suitable protective groups: Aloc, Pyoc, Fmoc, Tcboc, Z, Boc, Ddz, Bpoc, Adoc, Msc, Moc, Z($NO_2$), Z($Hal_n$), Bobz, Iboc, Adpoc, Mboc, Acm, tert-butyl, OBzl, ONbzl, OMbzl, Bzl, Mob, Pic, Trt and acetal groups and ketal groups, which latter two groups are protective groups for aldehyde and keto groups. Particular acetal and ketal groups include, for example geminal methoxy groups or ethoxy groups or ethylene-1,2-dioxy groups. Functional groups, which may be present in the residue R in addition to carboxylic acid groups and derivatives of carboxylic acid groups can be, for example, hydroxyl, $(C_1-C_4)$-alkoxy, $((C_1-C_4)$-alkyl)carbonyloxy, benzyloxy, oxo, amino, $((C_1-C_4)$-alkyl)carbonylamino such as acetylamino or isobutyrylamino, $((C_1-C_4)$-alkoxy)carbonylamino, such as tert-butoxycarbonylamino, benzyloxycarbonylamino, 9-fluorenylmethyloxycarbonylamino, mercapto, $(C_1-C_4)$-alkylmercapto, amidino, guanidino, etc., and protected forms of these groups.

Compounds of formula I that contain one or more basic groups may be present in the form of acid addition salts. Such basic groups include, for example, amino groups, guanidino groups or basic nitrogen heterocycles. Acid addition salts may be prepared from inorganic acids and organic acids. Suitable inorganic acids in preparing acid addition salts, include hydrogen chloride, hydrogen bromide, sulfuric acid or phosphoric acid. Suitable organic acids include, for example, organic carboxylic acids or sulfonic acids, such as, for example, acetic acid, trifluoroacetic acid, citric acid, benzoic acid, maleic acid, fumaric acid, tartaric acid, methanesulfonic acid or p-toluenesulfonic acid.

Compounds of formula I that contain one or more acidic groups may be present in the form of metal salts or ammonium salts. Such acidic groups include, for example, carboxylic acid groups. Preferred metal salts include, for example, alkali metal salts or alkaline earth metal salts. More preferred metal salts include, for example, lithium salts, sodium salts, potassium salts, magnesium salts or calcium salts. Ammonium salts include salts with quaternary ammonium ions and acid addition salts with ammonia and organic amines, such as, for example, ethylamine, triethylamine, ethanolamine, tris(2-hydroxyethyl)amine, α,α,α-tris(hydroxymethyl)methylamine or amino acids. Compounds of formula I that contain both acidic groups and basic groups may also be present in the form of inner salts or betaines (zwitterions), which are likewise encompassed by the present invention. Salts may be obtained from the compounds of formula I by conventional methods known to a person skilled in the art, for example, by combining with an organic or inorganic acid or base in a solvent or diluent, or by anion exchange or cation exchange from other salts.

The present invention encompasses the compounds of formula I in all their tautomeric forms. The invention further encompasses solvates of compounds of formula I, for example hydrates and adducts with alcohols.

The present invention encompasses all stereoisomeric forms of formula I, including enantiomers and diastereomers, as well as mixtures of two or more stereoisomeric forms, for example, mixtures of enantiomers and/or diastereomers, in all ratios. Compounds of formula I may contain one or more asymmetric centers, which may have, independently of one another, the S-configuration or R-configuration. Thus, the invention also relates to enantiomers in enantiomerically pure form (as levorotatory and as dextrorotatory antipodes), racemates and mixtures of the two enantiomers in all ratios. In addition, the invention relates to diastereomers in diastereomerically pure form, as well as mixtures of two or more diastereomers in all ratios. If a cis/trans isomerism is possible in the compounds of formula I (for example, if a double bond or a substituted cycloalkyl residue is present), the invention relates both to cis forms and trans forms, or Z forms and E forms, and mixtures thereof in all ratios. These statements apply correspondingly to the amino carboxylic acids and the amino carboxylic acid derivatives of the formula $H_2N$—R from which the residue R is derived and which may be present in all stereochemical forms, including the D form, the L form or the DL form. Individual stereoisomers can be prepared by using stereochemically pure starting materials in the synthesis, by stereoselective synthesis or by separating a mixture by conventional methods. Particular separation techniques include, for example, chromatography or crystallization, as well as chromatography on chiral phases for separating enantiomers. Stereoisomers may be derivatized before separation. A stereoisomer mixture may be separated at the stage of compounds of formula I or at the stage of a starting material or of an intermediate during the synthesis.

The following are examples of amino carboxylic acids from which or from whose derivatives the residue R may be derived (cf. Houben-Weyl, Methoden der organischen Chemie, volume 15/1 and 15/2, Georg Thieme Verlag, Stuttgart, 1974): Aad, Abu, γAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Bph, Can, Cit, Cys, Daad, Dab, Dadd, Dap, Dapm, Dasu, Dpa, Fel, Gln, Glu, Gly, hAla, hArg, hCys, hGln, hGlu, His, hIle, hLeu, hLys, hMet, hphe, hSer, hThr, hTrp, hTyr, Hyl, Ile, Ise, Iva, Kyn, Lant, Lcn, Leu, Lys, βLys, ALys, Met, nArg, Nle, Nva, Oly, Orn, Pan, Pen, Phe, Phg, Pse, Pya, Pza, Ros, Sec, Sem, Ser, Thi, βThi, Thr, Thy, Thx, Tle, Tly, Trp, Trta, Tyr, Val, tert-butylglycine (Tbg), neopentylglycine (Npg), cyclohexylglycine (Chg), cyclohexylalanine (Cha), 2-thienylalanine (Thia), 2,2-diphenylaminoacetic acid, 2-(p-tolyl)-2-phenylaminoacetic acid, 2-(p-chlorophenyl)aminoacetic acid, 3-aminobenzoic acid.

The residue R in formula I can be derived, for example, from an α-amino carboxylic acid, an α-amino carboxylic acid derivative or a salt thereof, a β-amino carboxylic acid, a β-amino carboxylic acid derivative or a salt thereof, a γ-amino carboxylic acid, a γ-amino carboxylic acid derivative or a salt thereof, an aromatic amino carboxylic acid, or an aromatic carboxylic acid derivative or a salt thereof. Preferably, residue R in formula I can be derived, for example, from an α-amino carboxylic acid, from an α-amino carboxylic acid derivative or a salt thereof, a β-amino carboxylic acid, a β-amino carboxylic acid derivative or a salt thereof. The residue R in formula I is more preferably derived from an α-amino carboxylic acid or an α-amino carboxylic acid derivative or a salt thereof. α-Amino carboxylic acids include compounds, which contain at least one amino group and at least one carboxylic acid group, of which one amino group and one carboxylic acid group are separated from one another by one carbon atom. β-Amino carboxylic acids include compounds, which contain at least one amino group and at least one carboxylic acid group, of which one amino group and one carboxylic acid group are separated from one another by a chain of two carbon atoms. γ-Amino carboxylic acids include compounds, which contain at least one amino group and at least one carboxylic acid group, of which one amino group and one carboxylic acid group are separated from one another by a chain of three carbon atoms. Aromatic amino carboxylic acids include compounds, which contain at least one amino group and at least one carboxylic acid group, which are bonded to a carbocyclic or heterocyclic aromatic ring system.

The present invention thus encompasses compounds of formula Ia, formula Ib, formula Ic, formula Id, or derivatives or salts thereof. Preferably, the invention provides compounds of formula Ia or formula Ib, or a derivative or a salt thereof. More preferably, the invention provides compounds of formula Ia or a derivative or a salt thereof. The residues $C(R^1)(R^2)COOH$ in formula Ia, $C(R^1)(R^2)C(R^3)(R^4)COOH$ in formula Ib, $C(R^1)(R^2)C(R^3)(R^4)C(R^5)(R^6)COOH$ in formula Ib, and ArCOOH in formula Id, each bonded to the ring nitrogen atom, are subgeneric embodiments of the residue R, which is present in the compounds of general formula I.

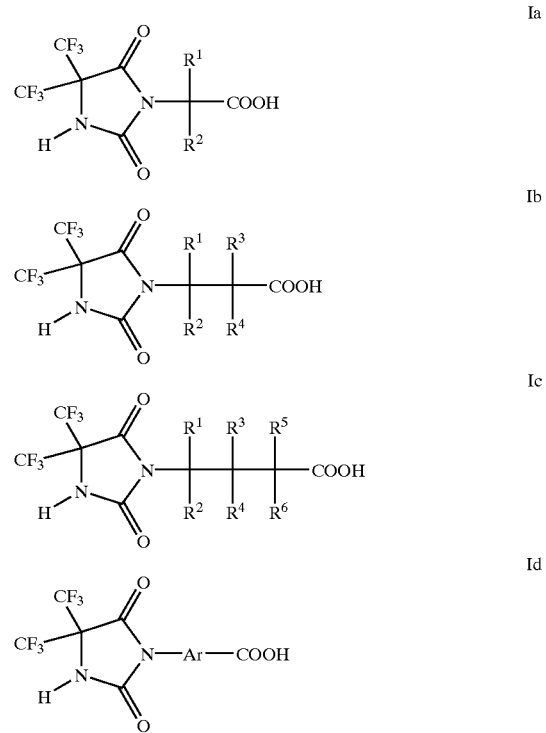

In formulae Ia, Ib and Ic, $R^1$, $R^2$, $R^3$, $R^4$, $R^5$ and $R^6$ are, independently of one another, selected from the group consisting of hydrogen, $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, $(C_6-C_{12})$-aryl, $(C_6-C_{12})$-aryl-$(C_1-C_4)$-alkyl, heteroaryl and heteroaryl-$(C_1-C_4)$-alkyl. It is also possible for $R^1$ and $R^2$, together with the carbon atom carrying these groups, or for $R^3$ and $R^4$, together with the carbon atom carrying these groups, or for $R^5$ and $R^6$, together with the carbon atom carrying these groups, to form a $(C_3-C_7)$-cycloalkane ring. It is also possible, for example, for $R^1$ and $R^3$, together with the carbon atoms carrying these groups, or for $R^3$ and $R^5$, together with the carbon atoms carrying these groups, to form a $(C_3-C_7)$-cycloalkane ring. The groups representing $R^1$, $R^2$, $R^3$, $R^4$, $R^5$ and $R^6$ may be unsubstituted or be substituted by one or more identical or different substituents. The divalent residue Ar in the compounds of formula Id is a residue of a monocyclic or polycyclic aromatic ring system, for example, of a monocyclic, bicyclic or tricyclic aromatic ring system having 5 to 15 ring members (e.g., 5, 6, 8, 9, 10, 11, 12, 13, 14 and 15 ring members), which can contain 1, 2, 3 or 4 identical or different ring heteroatoms selected from the group consisting of nitrogen, oxygen and sulfur. The groups representing Ar may be unsubstituted or be substituted by one or more identical or different substituents.

Derivatives of the compounds of the formulae Ia, Ib, Ic and Id are compounds wherein the carboxylic acid groups shown in formulae Ia, Ib, Ic and Id, and/or other carboxylic acid groups present in these molecules, are converted into other functional groups, preferably ester groups, amide groups, nitrile groups, aldehyde groups or hydroxymethyl groups, and more preferably ester groups.

Alkyl groups, alkenyl groups and alkynyl groups may be straight-chain or branched. Alkyl groups include, for example, methyl, ethyl, n-propyl, isopropyl (=1-methylethyl), n-butyl, sec-butyl (=1-methylpropyl), isobutyl (=2-methylpropyl), tert-butyl (=2,2-dimethylpropyl), n-pentyl, 1-methylbutyl, isopentyl, neopentyl, tert-pentyl, n-hexyl and isohexyl. Alkenyl and alkynyl groups include, for example, vinyl, prop-2-enyl (allyl), prop-1-enyl, but-2-enyl, but-3-enyl, 3-methylbut-2-enyl, penta-2,4-dienyl, ethynyl, prop-2-ynyl (propargyl), prop-1-ynyl, but-2-ynyl and but-3-ynyl. Cycloalkyl groups include, for example, cyclopropyl, cyclobutyl, cyclopentyl, cyclohexyl and cycloheptyl. Cycloalkylalkyl residues are include of example, cyclopropylmethyl, 1-cyclopropylethyl, 2-cyclopropylethyl, 3-cyclopropylpropyl, 4-cyclopropylbutyl, cyclobutylmethyl, 2-cyclobutylethyl, cyclopentylmethyl, 1-cyclopentylethyl, 2-cyclopentylethyl, 3-cyclopentylpropyl, cyclohexylmethyl, 1-cyclohexylethyl, 2-cyclohexylethyl, 3-cyclohexylpropyl, cycloheptylmethyl, and 2-cycloheptylethyl.

Examples of aryl groups are phenyl, 1-naphthyl, 2-naphthyl, 2-biphenylyl, 3-biphenylyl and 4-biphenylyl, and preferably phenyl. Heteroaryl groups are preferably derived from monocyclic 5-membered or 6-membered aromatic ring systems or bicyclic 9-membered or 10-membered aromatic ring systems, which contain 1, 2 or 3 identical or different heteroatoms from the series nitrogen, oxygen and sulfur, in particular from monocyclic 5-membered or 6-membered aromatic ring systems. Examples of heteroaryl are furyl, thienyl, pyrrolyl, imidazolyl, pyrazolyl, 1,3-oxazolyl, 1,2-oxazolyl, 1,3-thiazolyl, 1,2-thiazolyl, triazolyl, pyridyl, pyrazinyl, pyrimidyl, pyridazinyl, indolyl, benzofuranyl, benzothienyl, benzimidazolyl, 1,3-benzoxazolyl, 1,3-benzothiazolyl, quinolinyl, isoquinolinyl, quinazolinyl, or quinoxalinyl, etc. A heteroaryl residue may be bonded via any suitable position. For example, a thienyl residue may be present in the form of the 2-thienyl residue or 3-thienyl residue; a furyl residue may be present in the form of the 2-furyl residue or 3-furyl residue; and a pyridyl residue may be present in the form of the 2-pyridyl residue, 3-pyridyl residue or 4-pyridyl residue. A residue derived from 1,3-thiazole or imidazole may be bonded via the 2-position, 4-position or 5-position; and a residue derived from quinoline may be bonded via the 2-position, 3-position, 4-position, 5-position, 6-position, 7-position, or 8-position. Examples of arylalkyl residues are benzyl, 1-phenylethyl, 2-phenylethyl, 3-phenylpropyl, 4-phenylbutyl, (1-naphthyl)methyl, (2-naphthyl)methyl, 1-(1-naphthyl)ethyl, 1-(2-naphthyl)ethyl, 2-(1-naphthyl)ethyl, 2-(2-naphthyl)ethyl, (2-biphenylyl)methyl, (3-biphenylyl)methyl, and (4-biphenylyl)methyl. Examples of heteroarylalkyl residues are (2-pyridyl)methyl, (3-pyridyl)methyl, (4-pyridyl)methyl, 2-(2-pyridyl)ethyl, 2-(3-pyridyl)ethyl, 2-(4-pyridyl)ethyl, (2-thienyl)methyl, (3-thienyl)methyl, 2-(2-thienyl)ethyl, 2-(3-thienyl)ethyl, (4-imidazolyl)methyl, and (3-indolyl)methyl.

The above definitions of aryl groups and heteroaryl groups also apply to the divalent group Ar of formula Id, which is derived from a carbocyclic or heterocyclic aromatic ring system. The residue Ar may, for example, be derived from the aromatic residues listed above. Examples of the divalent residue Ar include phenylene, biphenylene (biphenyldiyl), naphthylene (naphthalenediyl), fluorenylene (fluorenediyl), anthracenediyl, thiophenediyl, furandiyl, pyrrolediyl, pyrazolediyl, imidazolediyl, thiazolediyl, pyridinediyl, pyridazinediyl, pyrimidinediyl, pyrazinediyl, indolediyl, benzothiophenediyl, quinolinediyl, isoquinolinediyl, carbazolediyl, and phenothiazinediyl. The residue Ar may be bonded via any suitable positions of the aromatic ring system. For example, a phenylene residue may be a 1,2-, 1,3- or 1,4-phenylene residue; a naphthalenediyl residue maybe a 1,2-, 1,3-, 1,4-, 1,5-, 1,6-, 1,7-, 1,8-, 2,3-, 2,6- or 2,7-naphthalenediyl residue; a thiophenediyl residue may be a 2,3-, 2,4-, 2,5- or 3,4-thiophenediyl residue; and a pyridinediyl residue may be a 2,3-, 2,4-, 2,5-, 2,6-, 3,4- or 3,5-pyridinediyl residue.

The alkyl, alkenyl, alkynyl, cycloalkyl, cycloalkylalkyl, aryl, arylalkyl, heteroaryl and heteroarylalkyl groups representing $R^1$, $R^2$, $R^3$, $R^4$, $R^5$ and $R^6$ may be unsubstituted or carry one or more, (e.g., one, two, three or four) identical or different substituents. In the case of substituted cycloalkylalkyl, arylalkyl and heteroarylalkyl groups, the substituents are preferably present in the cyclic moiety. Besides carboxylic acid groups (hydroxycarbonyl groups, carboxyl groups, COOH groups) and derivatives of carboxylic acid groups, such as ester groups, amide groups, nitrile groups (cyano groups), aldehyde groups (CH(=O) groups) or hydroxymethyl groups (primary alcohol groups, $CH_2OH$ groups), possible substituents, which may be present in $R^1$, $R^2$, $R^3$, $R^4$, $R^5$ and $R^6$ are, for example, halogen, trifluoromethyl, hydroxyl, $(C_1-C_4)$-alkoxy, benzyloxy, oxo, nitro, amino, $((C_1-C_4)$-alkyl)carbonylamino, $((C_1-C_4)$-alkoxy)carbonylamino, 9-fluorenylmethyloxycarbonylamino, benzyloxycarbonylamino, mercapto, $(C_1-C_4)$-alkylmercapto, amidino, guanidino, etc. Halogen substituents include fluorine and chlorine. It is also possible for the substituent groups to be present in protected form. Cycloalkyl groups, aryl groups and heteroaryl groups may also carry $(C_1-C_4)$-alkyl residues, for example, methyl residues, as substituents. The substituents in substituted residues may be present in any suitable positions as long as the resulting compound is stable and suitable for the desired purpose. The substituent in mono substituted phenyl residues may be present in the 2-position, the 3-position or the 4-position. The substituents in disubstituted phenyl residues may be present in the 2,3-position, 2,4-position, 2,5-position, 2,6-position, 3,4-position or 3,5-position. The above explanations apply correspondingly to substituents that may be present in the residue Ar. Ar may, for example, be substituted by one, two, three or four identical or different substituents selected from the group consisting of COOH, ester groups (e.g., $((C_1-C_6)$-alkoxy)carbonyl), amide groups (e.g., $CONH_2$), cyano, CH(=O), $CH_2OH$, $(C_1-C_4)$-alkyl, fluorine, chlorine, trifluoromethyl, hydroxyl, $(C_1-C_4)$-alkoxy, benzyloxy, nitro, amino, $((C_1-C_4)$-alkyl)carbonylamino, $((C_1-C_4)$-alkoxy)carbonylamino, $(C_1-C_4)$-alkylmercapto, and protected forms thereof.

$R^2$ is preferably hydrogen or methyl in formula Ia. In formula Ib, $R^2$ and/or $R^3$ and/or $R^4$ groups are, independently of one another, preferably hydrogen or methyl; or $R^1$ and/or $R^2$ and/or $R^4$ groups are, independently of one another, hydrogen or methyl. In the compounds of formula Ic, $R^2$ and/or $R^3$ and/or $R^4$ and/or $R^5$ and/or $R^6$ groups are, independently of one another, preferably hydrogen or methyl; or the $R^1$ and/or $R^2$ and/or $R^4$ and/or $R^5$ and/or $R^6$ groups are, independently of one another, hydrogen or methyl; or the $R^1$ and/or $R^2$ and/or $R^3$ and/or $R^4$ and/or $R^6$ groups are, independently of one another, hydrogen or methyl. The Ar group in the compounds of formula Id is preferably a divalent residue of a 5-membered or 6-membered monocyclic aromatic ring system or of a 9-membered or 10-membered bicyclic aromatic ring system, which can contain 1 or 2 identical or different ring heteroatoms selected from the group consisting of nitrogen, oxygen and sulfur.

In preferred embodiments, $R^2$ is preferably hydrogen in formula Ia. In other preferred embodiments, $R^2$, $R^3$ and $R^4$ groups in formula Ib are hydrogen; or the $R^5$, $R^2$ and $R^4$ groups are hydrogen. In other preferred embodiments, $R^2$, $R^3$, $R^4$, $R^5$ and $R^6$ groups in formula Ic are hydrogen; $R^1$, $R^2$, $R^4$, $R^5$ and $R^6$ groups are hydrogen; or $R^1$, $R^2$, $R^3$, $R^4$ and $R^6$ groups are hydrogen. In other preferred embodiments, Ar group in the compounds of formula Id is a divalent residue of a 5-membered or 6-membered monocyclic aromatic ring system, which can contain 1 or 2 identical or different ring heteroatoms from the series nitrogen, oxygen and sulfur, for example, a phenylene residue or a thiophenediyl residue.

A particularly preferred embodiment of the present invention encompasses a compound of formula Ie or a derivative or salt thereof.

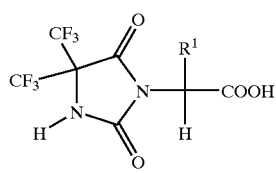

Ie $R^1$ in formula Ie has the meanings, and may be substituted, as indicated above. Derivatives of compounds of formula Ie include compounds wherein the carboxylic acid group depicted in formula Ie, and/or other carboxylic acid groups present in the molecule, are converted into other functional groups, such as ester groups, amide groups, nitrile groups, aldehyde groups or hydroxymethyl groups, and in particular, ester groups.

The residue —$CHR^1$—COOH of formula Ie is derived formally from an α-amino carboxylic acid of the formula $H_2N$—$CHR^1$—COOH by removal of the $H_2N$ group. $R^1$ corresponds to the side chain of the α-amino carboxylic acid, according to a usual way of viewing the $R^1$ residue in the compounds of formula Ie and in the amino carboxylic acids of the formula $H_2N$—$CHR^1$—COOH. Examples of such side chains and of the $R^1$ residue in formula Ie are alkyl residues, (e.g., methyl, isopropyl and isobutyl side chains present in alanine, valine or leucine), the cyclopropylmethyl side chain present in β-cyclopropylalanine, the benzyl side chain present in phenylalanine, the phenyl side chain present in phenylglycine, the 4-aminobutyl side chain present in lysine or the hydroxycarbonylmethyl side chain present in aspartic acid. Functional groups in the side chain of the α-amino carboxylic acid, from which the —$CHR^1$—COOH residue in the compounds of formula Ie may be derived, may be present in protected form.

$R^1$ in the compounds of the formulae Ia, Ib, Ic and Ie is preferably hydrogen, $(C_1-C_6)$-alkyl, $(C_3-C_7)$-cycloalkyl or $(C_3-C_7)$-cycloakyl-$(C_1-C_4)$-alkyl; more preferably $(C_1-C_6)$-alkyl, $(C_3-C_7)$-cycloalkyl, $(C_3-C_7)$-cycloalkyl-$(C_1-C_4)$-alkyl; and most preferably $(C_1-C_6)$-alkyl or $(C_3-C_6)$-cycloalkyl-$(C_1-C_2)$-alkyl, in particular $(C_3-C_5)$-alkyl or $(C_3-C_6)$-cyCloalkyl-$(C_1-C_2)$-alkyl. Specific examples of most preferred $R^1$, in particular in the compounds of formula Ie, are isopropyl (($CH_3)_2CH$—), isobutyl (($CH_3)_2CH$—$CH_2$—), neopentyl (($CH_3)_3C$—$CH_2$—), cyclopropylmethyl (cyclo$C_3H_5$—$CH_2$—), cyclobutylmethyl (cyclo$C_4H_7$—$CH_2$—) and cyclopentylmethyl (cyclo$C_5H_9CH_2$—), specifically isobutyl and cyclopropylmethyl. The asymmetric carbon atom to which the $R^1$ group is bonded in compounds of formula Ie preferably has the S configuration.

Compounds of formula I of the invention can be prepared by reacting the compound of formula II with a compound of formula III.

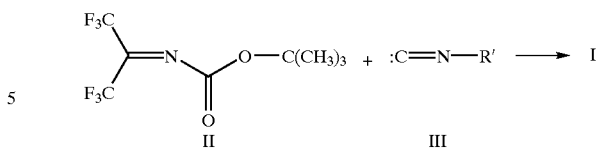

The R' residue in formula III has the meanings stated above for the R residue in formula I, but free carboxylic acid groups are present in the compounds of formula III in esterified form, for example, in the form of the $(C_1-C_6)$-alkyl esters or benzyl esters, including tert-butyl esters. Other functional groups, for example aldehyde groups or hydroxymethyl groups, may be or must be present in protected form or in the form of precursors, as already explained above for compounds of formula I. Examples of precursors are nitro groups, which can be converted into amino groups by reduction in a later step; or nitrile groups, which can be converted into aminomethyl groups by reduction or into amide groups or carboxylic acid groups by hydrolysis in a later step. Such protective group techniques and synthetic strategies for avoiding unwanted reactions taking place or for preventing side reactions are familiar to a person skilled in the art.

The present invention also encompasses a process for preparing the compounds of formula I, which comprises reacting the compound of formula II with a compound of formula III.

It is subsequently possible to modify functional groups in the compounds of formula I obtained as direct products of the reaction of compounds of the formulae II and III. For example, ester groups can be converted into carboxylic acid groups by methods known to one of ordinary skill in the art, such as by hydrolysis with an acid (e.g., hydrochloric acid) or, in the case of tert-butyl esters, by treating with trifluoroacetic acid. It is also possible for an ester group of a particular type, for example a tert-butyl ester, to be selectively converted into a carboxylic acid group, while a different ester group, for example an ethyl ester, to be left unchanged. A further example, which may be mentioned is the liberation of protected aldehyde groups or hydroxymethyl groups. Depending on the intended use, it may be advantageous for further protective groups in the resulting compounds of formula I to be removed before further processing by standard methods and for the protected functional groups thus to be liberated again, or for protective groups initially to be retained on functional groups and be removed only after the further processing.

The reaction of compounds of the formulae II and III is advantageously carried out in an inert solvent, such as a hydrocarbon or ether (e.g., benzene or toluene), generally at temperatures from about 20° C. to about 80° C. In one embodiment, the reaction mixture is heated to a temperature of from about 40° C. to about 80° C., preferably from about 50° C. to about 70° C., after the reactants have been combined. For workup, the volatile components can be removed in vacuo and the crude product of formula I can be purified by standard methods (e.g., chromatography).

The 2-tert-butoxy-4,4-bis(trifluoromethyl)-1,3-oxazabuta-1,3-diene of formula II can be obtained by the method described by Steglich et al., *Chemische Berichte* 107:1488 (1974). The starting materials are tert-butyl carbamate (($CH_3)_3C$—O—CO—$NH_2$) and anhydrous hexafluoroacetone, which are initially reacted, for example, in a solvent such as dichloromethane at room temperature, to give 2-tert-butoxycarbonylamino-2-hydroxy-1,1,1,3,3,3- hexafluoropropane. This intermediate is then converted, for example, in a solvent such as diethyl ether at temperatures from about 0° C. to about 10° C., by treatment with trifluoroacetic anhydride in the presence of a base (e.g., quinoline), into the compound of formula II, which can be purified by distillation. Details of the preparation are described below.

Isocyanides (i.e., isonitriles) of formula III can be obtained, by standard methods known to a person skilled in the art, from the respective amino carboxylic acid derivatives of the formula H$_2$N—R', wherein R' is defined above for formula III. The amino carboxylic acid derivative of the formula H$_2$N—R' is advantageously first converted by reaction with a reactive formic ester (e.g., cyanomethyl formate) into a N-formylamino carboxylic acid derivative of formula HC(=O)—NH—R', wherein R' has the meaning indicated for formula III. This N-formylamino carboxylic derivative is then converted into the isocyanide of formula III, for example, by further reaction with phosgene or a phosgene equivalent (e.g., diphosgene or triphosgene) in the presence of a tertiary amine (e.g., triethylamine) in a solvent (e.g., dichloromethane) at temperatures from about −40° C. to about 0° C.

The compounds of formula I are valuable intermediates for preparing pharmaceutically active compounds comprising a 2,5-dioxo-4,4-bis(trifluoromethyl)imidazolidine ring, wherein the 1-position is bonded to a structural element obtained formally from an amino carboxylic acid or an amino carboxylic acid derivative by removal of an amino group; and wherein the 3-position may optionally carry an additional substituent. Examples of such pharmaceutically active compounds are antagonists of the integrin VLA-4 as described, for example, in U.S. Pat. No. 6,331,552 B, EP-A-918059 or WO-A-99/60015 and can be represented by formula IV:

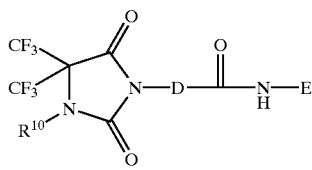

IV wherein the divalent residue —D—CO— is a residue of an amino carboxylic acid or amino carboxylic acid derivative, which is obtained formally by removal of an NH$_2$ group from an amino carboxylic acid and by removal of the hydroxyl group from the carboxylic acid group; the residue —NH—E is the residue of an amino compound (e.g., amino acid, an amino acid ester, a dipeptide or an amino alcohol), which is obtained formally by removal of a hydrogen atom from an amino group; and R$^{10}$ is, for example, an optionally substituted arylalkyl residue (e.g., substituted benzyl residue).

Compounds of formula I can be converted into a pharmaceutically active compound by first introducing a substituent on the nitrogen atom in the 3 position, such by an alkylation with a halogen compound (e.g., substituted benzyl chloride or benzyl bromide) in the presence of a base, and subsequently, where appropriate after removal of protective groups, reacting a functional group present in the R residue, for example a carboxylic acid group or a derivative thereof such as an ester group, amide group, nitrile group, aldehyde group or hydroxymethyl group, with a further synthetic building block. A compound of formula IV is preferably synthesized by employing a compound of formula I, wherein R contains a carboxylic acid group, and which is reacted under standard conditions in the presence of a condensing reagent, known to one of ordinary skill in peptide chemistry, for generating amide bonds (e.g., TOTU or a carbodiimide, such as N,N'-dicyclohexylcarbodiimide), with a compound of the formula H$_2$N—E (e.g., example an amino acid ester or an amino alcohol). An example of such a reaction to give a pharmaceutically active ingredient is described below.

The present invention encompasses the use of the compounds of formula I as intermediates, in particular for preparing pharmaceutically active ingredients, as well as a process for preparing pharmaceutically active ingredients. In particular, the pharmaceutically active ingredients comprise a 2,5-dioxo-4,4-bis(trifluoromethyl)imidazolidine ring, wherein the 1-position is bonded to a synthetic building block, which is obtained formally from an amino carboxylic acid or an amino carboxylic acid derivative by removal of an amino group, and whose 3-position may optionally carry an additional substituent. The process of preparing such compounds of formula I comprises reacting a functional group, which is present or liberated in the residue R in formula I, for example the carboxylic acid group or a derivative thereof, which is present in the residue R, with a further synthetic building block and optionally introducing an additional substituent in the 3-position.

EXAMPLES

Example 1

Tert-Butyl (S)-2-(4,4-bis(trifluoromethyl)-2,5-dioxoimidazolidin-1-yl)-2-(2-methylpropyl)acetate

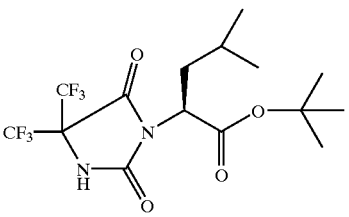

1a) 2-tert-Butoxy-4,4-bis(trifluoromethyl)-1,3-oxazabuta-1,3-diene

The compound was prepared in analogy to W. Steglich et al., Chem. Ber., 107:1488–1498 (1974). Anhydrous hexafluoroacetone (HFA) was prepared by adding HFA trihydrate dropwise to concentrated sulfuric acid heated to 80° C. The resulting gas was once more washed with concentrated sulfuric acid and then passed into the gas space of the reaction flask. A reflux condenser packed with acetone/dry ice was fitted on the gas outlet of the flask.

As described above, a solution of 20 g (170 mmol) of tert-butyl carbamate in 150 mL of dichloromethane was reacted with anhydrous gaseous HFA until the reaction solution was saturated. The solvent was removed in vacuo, and the resulting crude 2-tert-butoxycarbonylamino-2-hydroxy-1,1,1,3,3,3-hexafluoropropane (yield: 48.3 g, 100%) was used in the subsequent reaction.

13.6 g of trifluoroacetic anhydride, and subsequently 5 drops of quinoline, were added dropwise to a solution of 50.05 g (176 mmol) of 2-tert-butoxycarbonylamino-2-hydroxy-1,1,1,3,3,3-hexafluoropropane in 300 mL of diethyl ether at 0° C. After stirring at 0° C. for 10 minutes, a further 27.2 g of trifluoroacetic anhydride were added dropwise. The reaction mixture was stirred at 0° C. (external temperature) for 30 minutes, during which the internal temperature of the mixture rose to 8-10 C. After cooling to 0° C., 50.01 g (388 mmol) of quinoline were added, whereupon the trifluoroacetic acid salt of the quinoline started to crystallize. After stirring at 0° C. for 2 hours the mixture was filtered. Residual salt was removed from the filtrate by distilling it in vacuo into a receiver flask cooled with acetone/dry ice. The distillate was then distilled through a Vigreux column. 36.2 g (77%) of the title compound were obtained. Boiling point: 126–130° C.

$^1$H NMR (CDCl$_3$): δ 1.82 ppm (s; O—C(CH$_3$)$_3$)

$^{19}$F NMR (CDCl$_3$): δ-10.86 ppm (br. s, CF$_3$), δ-7.53 ppm (br. s, CF$_3$)

1b) N-Formyl-L-leucine tert-butyl ester

The preparation was performed in analogy to W. Duczek et al., Synthesis, 37–38 (1996). A solution of 4.04 g (40 mmol) of triethylamine in 10 mL of dichloromethane was added to a solution of 8.94 g (40 mmol) of L-leucine tert-butyl ester hydrochloride and 3.4 g (40 mmol) of cyanomethyl formate in 60 mL of dichloromethane at 0° C. The reaction solution was allowed to warm to room temperature, stirred at room temperature overnight, and then washed twice with saturated NaCl solution. The phases were separated and the organic phase was dried over magnesium sulfate. The residue obtained after filtration and removal of the solvent in vacuo was distilled in vacuo. Yield: 7.5 g (87%). Boiling point: 118° C./2.7 Pa (0.02 torr).

$^1$H NMR (CDCl$_3$): δ 0.84 (d, 3H, CH$_3$), δ 0.87 (d, 3H, CH$_3$), δ 1.36 (s, 9H, C(CH$_3$)$_3$). δ 1.49 (m, 3H, CH, CH$_2$), δ 4.51 (m, 1H, N—CH), δ 6.75 (br. s, 1H, NH), δ 8.10 ppm (s. 1H, CH(O))

1c) Tert-Butyl (S)-2-(4,4-bis(trifluoromethyl)-2,5-dioxoimidazolidin-1-yl)-2-(2-(2methylpropyl)acete 2.4 g (12.1 mmol) of diphosgene were added to a solution of 2.5 g (11.6 mmol) of N-formyl-L-leucine tert-butyl ester and 2.5 g (24.7 mmol) of triethylamine in 100 ml of dry dichloromethane at −30° C. The reaction solution was allowed to warm to −10° C. over the course of 1 hour and was stirred further at this temperature until the reaction was complete. The reaction solution was then washed at room temperature twice with 7% strength sodium hydrogencarbonate solution. The phases were separated and the organic phase was dried over magnesium sulfate. After filtration, the solvent was removed in vacuo, and the residue was taken up in 70 mL of benzene. 3 g (11.3 mmol) of 2-tert-butoxy-4,4-bis(trifluoromethyl)-1,3-oxazabuta-1,3-diene in 10 ml of benzene were added dropwise to this solution at room temperature. The reaction solution was heated to 60° C. overnight and then benzene was removed in vacuo. Chromatography of the residue over silica gel (eluent:petroleum ether/ethyl acetate=10/1) resulted in 3.7 g (80%) of the title compound. Melting point: 105–106° C. [α]$^{20}$=−24° (c=1. CHCl$_3$).

$^1$H NMR (CDCl$_3$): δ 0.88 (d, 3H, CH$_3$), δ 0.92 (d, 3H, CH$_3$), δ 1.32 (m, 1H, CH), δ 1.41 (s, 9H, (CH$_3$)$_3$), δ 1.83 (m, 1H, CH$_2$), δ 2.16 (m, 1H, CH$_2$), δ 4.64 (dd, 1H, N—CH), δ 7.93 ppm (br. s, 1H, NH).

$^{19}$F NMR (CDCl$_3$): δ 4.8 ppm (m)

$^{13}$C NMR (CDCl$_3$): δ 20.95, δ 23.41, δ 25.20, δ 27.99, δ 36.68, δ 53.35, δ 66.39 (sept, C—CF$_3$, J$_{C-F}$=32.0 Hz), δ 83.97, δ 120.49 q (CF$_3$, J$_{C-F}$=286.5 Hz), δ 156.18, δ 106.54, δ 167.52 ppm.

Example 2

(S)-2-(4,4-Bis(trifluoromethyl)-2,5-dioxoimidazolidin-1-yl)-2-(2-methylpropyl)acetic Acid

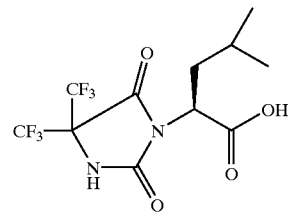

A solution of 7 g (117.2 mmol) of the compound of example 11c) in 20 mL of dichloromethane were added to a mixture of 30 mL of trifluoroacetic acid and 50 mL of dichloromethane at 10° C., and the reaction mixture was stirred at room temperature for 16 hours. Removal of trifluoroacetic acid and dichloromethane in vacuo resulted in 6.0 g (99%) of the title compound. Melting point: 154–156° C. [α]$^{22}$=−23° (c=2, methanol).

$^1$H NMR (CD$_3$OD): δ 0.92 (m, 6H, (CH$_3$)$_2$), δ 1.41 (m, 1H, CH), δ 1.84 (m, 1H, CH$_2$), δ 2.23 (m, 1H, CH$_2$), δ 4.71 ppm (m, 1H, N—CH)

$^{19}$F NMR (CDCl$_3$): δ 3.9 ppm (m).

Example 3

Tert-Butyl (S)-2-(4,4-bis(trifluoromethyl)-2,5-dioxoimidazolidin-1-yl)-2-(cyclopropylmethyl)acetate

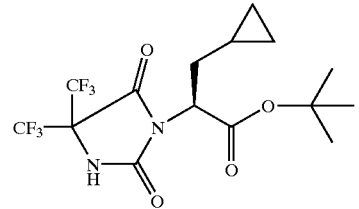

3a) (S)-β-Cyclopropylalanine tert-butyl ester 3.5 g (27.1 mmol) of (S)-β-cyclopropylalanine were added to a mixture of 50 mL of dioxane and 5 ml of concentrated sulfuric acid (prepared by cautious addition of the acid dropwise to dioxane at 5° C.) at room temperature. The solution was transferred into a sealing tube into which 40 ml of isobutylene were condensed at −78° C. The sealed tube was then shaken at room temperature on a shaker for 24 hours. After the sealed tube had been opened (while cooling), the reaction mixture was cautiously introduced into a stirred mixture of 30 mL of triethylamine and 50 mL of water cooled to 0° C. After removal of excess isobutylene, the product was extracted with ether (2×50 mL). Drying of the ether phases over magnesium sulfate, filtration and removal of the solvent in vacuo resulted in the crude product (pale yellow oil), which was employed without further purification in the subsequent reaction. Yield 4.2 g (84%).

$^1$H NMR (CDCl$_3$): δ 0.10 (m, 2H, CH$_2$), δ 0.49 (m, 2H, CH$_2$), δ 0.81 (m, 1H, CH), δ 1.25 (br. m, 2H, NH$_2$), δ 1.50 (s, 9H, (CH$_3$)$_3$), δ 1.61 (m, 2H, CH$_2$), δ 3.41 ppm (dd, 1H, N—CH)

3b) (S)-N-Formyl-β-cyclopropylalanine tert-butyl ester

A mixture of 10 g (54 mmol) of (S)-β-cyclopropylalanine tert-butyl ester and 4.7 g (55.2 mmol) of cyanomethyl formate in 100 mL of dichloromethane was stirred at room temperature overnight. The residue obtained after removal of the solvent in vacuo was distilled in vacuo. Yield: 8.8 g (76%). Boiling point 120° C./40 Pa (0.3 torr).

$^1$H NMR (CDCl$_3$): δ 0.09 (m, 2H, CH$_2$), δ 0.48 (m, 2H, CH$_2$), δ 0.65 (m, 1H, CH), δ 1.47 (s, 9H, (CH$_3$)$_3$), δ 1.69 (m, 2H, CH$_2$), δ 4.63 (m, 1H, N—CH), δ 6.31 (1H, NH), δ 8.20 ppm (s, 1H, CH(O)).

3c) tert-butyl (S)-2-(4,4-bis(trifluoromethyl)-2,5-dioxoimidazolidin-1-yl)-2-(cyclopropylmethyl)acetate 2.4 g (12.1 mmol) of diphosgene were added to a solution of 2.5 g (11.7 mmol) of (S)-N-formyl-β-cyclopropylalanine tert-butyl ester and 2.5 g (24.7 mmol) of triethylamine in 100 mL of dry dichloromethane at −30° C. The reaction solution was allowed to warm to −15° C. over the course of 1 hour and was stirred further at this temperature until the reaction was complete. The reaction solution was then washed at room temperature twice with 7% strength sodium hydrogencarbonate solution, and the organic phase was dried over magnesium sulfate. After filtration, the solvent was removed in vacuo, and the residue was taken up in 70 mL of benzene. 3.05 g (11.5 mmol) of 2-tert-butoxy-4,4-bis(trifluoromethyl)-1,3-oxazabuta-1,3-diene in 10 mL of benzene were added dropwise at room temperature to this solution. The reaction solution was heated to 60° C. overnight and then benzene was removed in vacuo. The residue was chromatographed over silica gel (eluent:petroleum ether/ethyl acetate=8/1). Yield: 3.7 g (78%). Melting point: 76–77° C. [α]$^{20}$=−28° (c=1, CHCl$_3$).

$^1$H NMR (CDCl$_3$): δ 0.08 (m, 2H, CH$_2$), δ 0.42 (m, 2H, CH$_2$), δ 0.50 (m, 1H, CH), δ 1.40 (s, 9H, (CH$_3$)$_3$), δ 2.02 (m, 2H, CH$_2$), δ 4.67 (dd, 1H, N—CH), δ 7.73 ppm (s, 1H, NH).

$^{19}$F NMR (CDCl$_3$): δ 4.89 ppm (m).

$^{13}$C NMR (CDCl$_3$): δ 3.46, δ 5.21, δ 7.76, δ 27.99, δ 32.96, δ 55.41, δ 66.48 (sept, C—CF$_3$, J$_{C—F}$=32.0 Hz), δ 83.94, δ 120.49 (q, CF$_3$, J$_{C—F}$=286.5 Hz), δ 156.19, δ 106.55, δ 166.96 ppm Example 4

(S)-2-(4,4-Bis(trifluoromethyl)-2,5-dioxoimidazolidin-1-yl)-2-(cyclopropylmethyl)acetic Acid

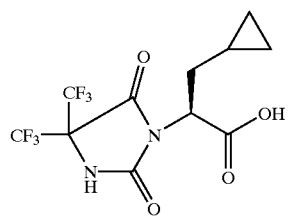

A solution of 7 g (117.3 mmol) of the compound of example 3c) in 20 mL of dichloromethane was added to a mixture of 30 mL of trifluoroacetic acid and 50 mL of dichloromethane at 10° C., and the mixture was stirred at room temperature for 16 hours. After removal of trifluoroacetic acid and dichloromethane in vacuo, 5.9 g (98%) of the title compound were obtained.

Melting point: 123–125° C., [α]$^{22}$=−26° (c=2, methanol).

$^1$H NMR (d$_6$-acetone): δ 0.40 (m, 2H, CH$_2$), δ 0.75 (m, 2H, CH$_2$), δ 0.92 (m, 1H, CH), δ 2.44 (m, 2H, CH$_2$), δ 5.15 (dd, 1H, N—CH), δ 9.85 ppm (s, 1H, CO$_2$H)

$^{19}$F NMR (d$_6$-acetone): δ 5.17 ppm (m).

Example 5 reaction to give the pharmaceutically active ingredient (S)-3-((S)-2-(4,4-Bis(trifluoromethyl)-3-(4-(3-(2-methylphenyl)ureido)-3-methoxybenzyl) -2,5-dioxoimidazolidin-1-yl)-2-(cyclopropylmethyl) acetylamino)-3-phenylpropionic Acid

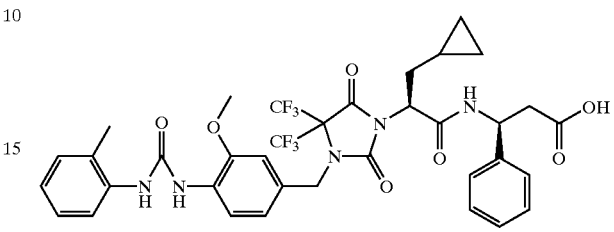

5a) 4-(3-(2-Methylphenyl)ureido)-3-methoxybenzyl Alcohol 15 g (81.8 mmol) of 3-methoxy-4-nitrobenzyl alcohol were hydrogenated in 500 mL of methyl tert-butyl ether over 1.3 g of palladium/carbon (10%; 50% water) while cooling in ice. After hydrogen uptake had ceased, the catalyst was filtered off, and 10.14 mL (81.8 mmol) of 2-methylphenyl isocyanate were added to the stirred filtrate over the course of 30 minutes. The reaction mixture was left to stand overnight, and the precipitated solid was filtered off with suction and washed with methyl tert-butyl ether. Yield: 20.5 g (88%).

5b) 4-(3-(2-Methylphenyl)ureido)-3-methoxybenzyl Chloride 7.65 mL (104.8 mmol) of thionyl chloride were added dropwise to a suspension of 15 g (52.4 mmol) of the compound of example 5a) in 300 mL of dichloromethane while cooling in ice. The reaction mixture was then stirred at room temperature for 3 hours, left to stand overnight and poured into 1000 mL of heptane. The heptane was decanted off from the oil, which had separated out, the residue was again suspended in heptane, and the heptane was decanted off. This procedure was repeated twice more. The residue was then dissolved in dichloromethane and poured into 800 mL of ice-cold diisopropyl ether. The mixture was then stirred while cooling in ice for 2 hours, and the product was filtered off with suction, washed with diisopropyl ether and dried over phosphorus pentoxide. Yield: 12 g (75%).

5c) (S)-2-(4,4-Bis(trifluoromethyl)-3-(4-(3-(2-methylphenyl)ureido)-3-methoxybenzyl-2,5-dioxoimidazolidin-1-yl)-2-(cyclopropylmethyl) Acetic Acid 3.2 mL of an n-butyllithium solution (2.5 M in hexane) were added to a solution of 1.39 g (4 mmol) of the compound of example 4) in 40 mL of absolute tetrahydrofuran (THF) under argon at −40° C. The reaction mixture was allowed to warm to 0° C. while stirring, a solution of 2.43 g (8 mmol) of 4-(3-(2-methylphenyl)ureido)-3-methoxybenzyl chloride in 20 mL of absolute THF was added, and the reaction mixture was stirred at room temperature for 3 hours. 20 mL of 1N hydrochloric acid were added and THF was removed in vacuo. The aqueous phase was extracted twice with methyl tert-butyl ether. The combined organic phases were dried over sodium sulfate and, after filtration, concentrated in vacuo. The residue was purified by preparative HPLC. Concentration of the product fractions and freeze drying resulted in 1.41 g (57%) of the title compound.

5d) Ethyl (S)-3-((S)-2-(4,4-bis(trifluoromethyl)-3-(4-(3-(2-methylphenyl) ureido)-3-methoxybenzyl)-2,5-dioxoimidazolidin-1-yl)-2-(cyclopropylmethyl) acetylamino)-3-phenylpropionate 748 mg (2.28 mmol) of TOTU (O-((cyano (ethoxycarbonyl)methylene)amino)-N,N,N',N'-tetramethyluronium tetrafluoroborate) and 368 μl of N,N-diisopropylethylamine were added to a solution of 1.41 g (2.28 mmol) of the compound of example 5c) and 442 mg (2.28 mmol) of ethyl (S)-3-amino-3-phenylpropionate in 20 mL of absolute dimethylformamide (DMF) at 0° C. After stirring at room temperature for 1 hour, the DMF was removed in vacuo, the residue was taken up in ethyl acetate, and the ethyl acetate solution was washed successively with an aqueous $KHSO_4/K_2SO_4$ solution, a saturated $NaHCO_3$ solution and water. The organic phase was dried over sodium sulfate and filtered. The solvent was then removed in vacuo, and the residue was chromatographed over silica gel with heptane/ethyl acetate (3/2). Concentration of the product fractions resulted in 1.48 g (82%) of the title compound.

5e) (S)-3-((S)-2-(4,4-Bis(trifluoromethyl)-3-(4-(3-(2-methylphenyl)ureido)-3-methoxybenzyl)-2,5-dioxoimidazolidin-1-yl)-2-(cyclopropylmethyl) acetylamino)-3-phenylpropionic Acid A solution of 1.46 g (1.84 mmol) of the compound of example 5d) in 40 mL of N-methyl-2-pyrrolidone and 20 mL of 6N hydrochloric acid was heated at 60° C. for 6 hours. After cooling to room temperature, the reaction mixture was poured into 300 mL of water, and the precipitate was filtered off with suction, washed with water and dried over phosphorus pentoxide. The crude product was chromatographed twice over silica gel (eluent:dichloromethane/methanol/acetic acid/water=95/5/0.5/0.5). After concentration of the product fractions, the residue was taken up in dichloromethane, and the organic phase was washed with water and dried over sodium sulfate. Filtration, removal of the solvent in vacuo and freeze drying resulted in 1.19 g (85%) of the title compound.

ES(+)-MS: 764.2 $(M+H)^+$.

What is claimed is:

1. A hydantoin having the formula:

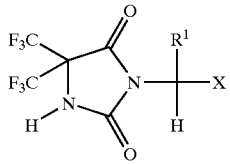

in any stereoisomeric or tautomeric form,
wherein $R^1$ is hydrogen or an unsubstituted or substituted residue selected from the group consisting of $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, $(C_6-C_{12})$-aryl, $(C_6-C_{12})$-aryl-$(C_1-C_4)$-alkyl, heteroaryl and heteroaryl-$(C_1-C_4)$-alkyl,
wherein X is COOH, a metal salt of COOH, an ammonium salt of COOH, a $C_1-C_6$ alkyl carboxylate ester, a benzyl carboxylate ester, —$CONH_2$, —CN, —CHO, or —$CH_2OH$.

2. The hydantoin of claim 1, wherein $R^1$ is $(C_1-C_6)$-alkyl, $(C_3-C_7)$-cycloalkyl or $(C_3-C_7)$-cycloalkyl-$(C_1-C_4)$-alkyl.

3. The hydantoin of claim 2, wherein $R^1$ is isobutyl or cyclopropylmethyl.

4. The hydantoin of claim 2, wherein the carbon atom carrying the $R^1$ residue has an S configuration.

5. The hydantoin of claim 1, wherein X is a $(C_1-C_6)$-alkyl carboxylate ester.

6. The hydantoin according to claim 1, wherein X is COOH, a metal salt of COOH, or an ammonium salt of COOH.

7. The hydantoin according to claim 1, wherein X is a $C_1-C_6$ carboxylate ester, a benzyl carboxylate ester, or —$CONH_2$.

8. A hydantoin having the formula:

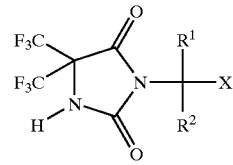

wherein $R^1$ and $R^2$ independently are selected from the group consisting of hydrogen or an unsubstituted or substituted residue selected from the group consisting of $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, $(C_6-C_{12})$-aryl, $(C_6-C_{12})$-aryl-$(C_1-C_4)$-alkyl, heteroaryl and heteroaryl-$(C_1-C_4)$-alkyl,
wherein X s COOH, a metal salt of COOH, an ammonium salt of COOH, a $C_1-C_6$ alkyl carboxylate ester, a benzyl carboxylate ester, —$CONH_2$, —CN, —CHO, or —$CH_2OH$.

9. The hydantoin according to claim 8, wherein X is COOH a metal s it of COOH, or an ammonium salt of COOH.

10. The hydantoin according to claim 8, wherein X is a $C_1-C_6$ alkyl carboxylate ester, a benzyl carboxylate ester, or —$CONH_2$.

11. The hydantoin of claim 8, wherein the X is a $(C_1-C_6)$-alkyl carboxylate ester.

12. A process for preparing a hydantoin according to claim 8, which comprises reacting the compound of formula II with a compound of formula III

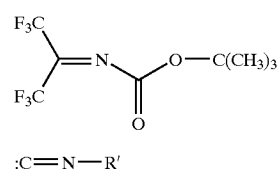

wherein R' is —$C(R^1)(R^2)$—X,
wherein $R^1$ and $R^2$ independently are selected from the group consisting of hydrogen or an unsubstituted or substituted residue selected from the group consisting of $(C_1-C_6)$-alkyl, $(C_2-C_6)$-alkenyl, $(C_2-C_6)$-alkynyl, $(C_3-C_7)$-cycloalkyl, $(C_3-C_7)$-cycloalkyl-$(C_1-C_4)$-alkyl, $(C_6-C_{12})$-aryl, $(C_6-C_{12})$-aryl-$(C_1-C_4)$-alkyl, heteroaryl and heteroaryl-$(C_1-C_4)$-alkyl, and
wherein X' is selected from the group consisting of a $C_1-C_6$ alkyl carboxylate ester, a benzyl carboxylate ester, —$CONH_2$, —CN, —CHO, or —$CH_2OH$.

13. The process of claim 12, wherein the reaction is carried out in an inert solvent and at a temperature from about 20° C. to about 80° C.

* * * * *

UNITED STATES PATENT AND TRADEMARK OFFICE
CERTIFICATE OF CORRECTION

PATENT NO. : 6,794,517 B2
DATED : September 21, 2004
INVENTOR(S) : Volkmar Wehner et al.

It is certified that error appears in the above-identified patent and that said Letters Patent is hereby corrected as shown below:

Column 18,
Line 27, delete "X s" and insert -- X is --.
Line 32, delete "COOH a metal s it of COOH," and insert -- COOH, a metal salt of COOH, --.
Line 37, after "wherein" delete "the".
Line 52, delete "X," and insert -- X', --.

Signed and Sealed this

Twenty-seventh Day of September, 2005

JON W. DUDAS
*Director of the United States Patent and Trademark Office*